United States Patent [19]

Sankey et al.

[11] Patent Number: 5,470,969
[45] Date of Patent: Nov. 28, 1995

[54] CATALYZED SUCROSE-6-ESTER PROCESS

[75] Inventors: George H. Sankey, Athens, Ga.; Nicholas M. Vernon, Durham, England; Robert E. Wingard, Jr., Athens, Ga.

[73] Assignee: McNeil-PPC, Inc., Milltown, N.J.

[21] Appl. No.: 237,947

[22] Filed: May 2, 1994

Related U.S. Application Data

[63] Continuation of Ser. No. 30,930, Mar. 12, 1993, abandoned, which is a continuation-in-part of Ser. No. 870,190, Apr. 13, 1992, abandoned, which is a continuation of Ser. No. 572,816, Aug. 27, 1990, abandoned.

[51] Int. Cl.$^6$ .................. C07H 1/00; C07H 13/02; C07H 15/04
[52] U.S. Cl. .................. 536/115; 536/116; 536/119; 536/120; 536/124
[58] Field of Search .................. 536/119, 120, 536/115, 116, 121, 124, 18.6, 18.2

[56] References Cited

U.S. PATENT DOCUMENTS

| | | | |
|---|---|---|---|
| 4,950,746 | 8/1990 | Navia | 536/119 |
| 4,980,463 | 12/1990 | Walkup et al. | 536/124 |
| 5,023,329 | 6/1991 | Neiditch et al. | 536/119 |

FOREIGN PATENT DOCUMENTS

| | | |
|---|---|---|
| 0352048 | 1/1990 | European Pat. Off. . |
| 62-87248 | 4/1987 | Japan . |
| 63-196544 | 8/1988 | Japan . |

OTHER PUBLICATIONS

Patent Abstracts of Japan, vol. 11, No. 297 (C–448) (2744) Sep. 25, 1987, and JP–A–62 087 248 (Kuraray Co Ltd) Apr. 21, 1987.
Patent Abstracts of Japan, vol. 12, No. 479 (C–552) (3326) Dec. 14, 1988, and JP–A–63 196 544 (Osaka Yuki Kagaku Kogyo K.K.) Aug. 15, 1988.
David et al., Regioselective Manipulation of Hydroxyl Groups via Organotin Derivatives, Tetrahedron, vol. 41, No. 4, pp. 643–663 (1985).
Wagner et al., J. Org. Chem., 39, 24 (1974).
Holzapfel et al., "Sucrose Derivatives and the Selective Benzoylation of the Secondary Hydroxyl Groups of 6,1', 6'-Tri-O-tritylsucrose", S. Afr. Tydskr. Chem, 1984, 37(3), pp. 57–61.
J. Otera, S. Ioka, and H. Nozaki, J. Org. Chem., 54, 4013 (1989).
J. Otera, T. Yano, A. Kawabata, and H. Nozaki, Tetrahedron Lett., 2383 (1986).
S. Schreiber and H. Meyers, J. Am. Chem. Soc., 110, 5198 (1988); and S. Schreiber, D. Desmaele, and J. Porco, Tetrahedron Lett., 6689 (1988).

Primary Examiner—Michael G. Wityshyn
Assistant Examiner—Everett White
Attorney, Agent, or Firm—Charles J. Metz

[57] ABSTRACT

Sucrose is mono-acylated in the 6-position by reacting sucrose with a carboxylic acid anhydride such as acetic or benzoic anhydride in a reaction mixture containing a polar aprotic solvent and a catalytic quantity of a 1,3-diacyloxy-1,1,3,3-tetra(hydrocarbyl)distannoxane, for a period of time and at a temperature sufficient to produce a sucrose-6-ester.

40 Claims, No Drawings

CATALYZED SUCROSE-6-ESTER PROCESS

CROSS-REFERENCE TO RELATED APPLICATIONS

This application is a continuation of application Ser. No. 08/030,930, filed Mar. 12, 1993, now abandoned, which was a continuation-in-part of application Ser. No. 07/870,190, filed Apr. 13, 1992, now abandoned, which in turn was a continuation of application Ser. No. 07/572,816, filed Aug. 27, 1990, now abandoned.

The invention relates to a process for the regioselective esterification of sucrose utilizing a distannoxane diester as a catalyst.

BACKGROUND OF THE INVENTION

The artificial sweetener 4,1',6'-trichloro-4,1',6'-trideoxygalactosucrose ("sucralose") is derived from sucrose by replacing the hydroxyls in the 4, 1', and 6' positions with chlorine (In the process of making the sweetener, the stereo configuration at the 4 position is reversed—hence the compound is a galactosucrose.) The direction of the chlorine atoms to only the desired positions is a major synthesis problem because the hydroxyls that are replaced are of differing reactivity; two are primary and one is secondary. The synthesis is further complicated by the fact that the primary hydroxyl in the 6 position is unsubstituted in the final product.

A number of different synthetic routes for the preparation of sucralose have been developed in which the reactive hydroxyl in the 6 position is first blocked, as by an ester group, prior to the chlorination of the hydroxyls in the 4, 1', and 6' positions, followed by hydrolysis to remove the ester substituent to produce sucralose. Several of such synthesis routes involve tin-mediated syntheses of sucrose-6-esters. Illustrative are the tin-mediated routes disclosed by Navia (U.S. Pat. No. 4,950,746), Neiditch et al. (U.S. Pat. No. 5,023,329), and Walkup et al. (U.S. Pat. No. 5,089,608).

BRIEF SUMMARY OF THE INVENTION

The process of the invention comprises reacting sucrose with a carboxylic acid anhydride in a reaction mixture comprising a polar aprotic solvent and a catalytic quantity of a 1,3-diacyloxy-1,1,3,3-tetra(hydrocarbyl)distannoxane ("distannoxane diester" or "DSDE"), for a period of time and at a temperature sufficient to produce a sucrose-6-ester.

THE PRIOR ART

The organotin-mediated regioselective 6-position acylations of sucrose to produce sucrose-6-esters are described in the Navia, Neiditch et al., and Walkup et al. patents referred to above. The utility of sucrose-6-esters in a process for producing the artificial sweetener 4,1',6'-trichloro-4,1',6'-trideoxygalactosucrose is described, for example, in the said Navia, Neiditch et al., and Walkup et al. patents, as well as in Walkup et al., IMPROVED SUCROSE-6-ESTER CHLORINATION, U.S. Pat. No. 4,980,463. A process for recovery of organotin esters from the processes of the Navia, Neiditch et al. and Walkup et al. processes is disclosed in Vernon et al., U.S. Pat. No. 5,034,551.

In a review article entitled REGIOSELECTIVE MANIPULATION OF HYDROXYL GROUPS VIA ORGANOTIN DERIVATIVES, *Tetrahedron*, Vol. 41, No. 4, pp 643–663 (1985), David et al. disclose the reaction of tin compounds with hydroxyl-group containing compounds to produce stannoxyl compounds, which can then be alkylated or acylated to produce ethers or esters. The reaction of bis(tributyltin) oxide with various carbohydrates (including sucrose), followed by acylation to produce a mixture of esters of varying degrees of substitution, is disclosed. The use of dibutyltin oxide in a reaction with carbohydrates is also disclosed in the article. The authors report the preparation of two dialkylstannylene carbohydrate derivatives, the 2,3-O-dibutylstannylene derivative of methyl 4,6-O-benzylidene-α-D-glucopyranoside and 4,6-O-benzylidene-2,3-O-dibutylstannylene-α-D-mannopyranoside. The proposed molecular structures of these two stannylene derivatives are shown in FIGS. 3 and 4 on page 645 of the article.

Wagner et al., *J. Org. Chem.*, 39, 24 (1974), disclose the preparation of dibutylstannylene derivatives of nucleosides by reacting dibutyltin oxide with nucleosides in refluxing methanol. After stripping off the methanol, the stannylene derivative was acylated by reaction with equimolar quantities of acid chloride and triethylamine.

Holzapfel et al., in "Sucrose Derivatives and the Selective Benzoylation of the Secondary Hydroxyl Groups of 6,1',6'-Tri-O-tritylsucrose", *S. Afr. Tydskr. Chem.*, 1984,37(3), pages 57–61, disclose the reaction of dibutyltin oxide with 6,1',6'-tri-O-tritylsucrose, followed by reaction with benzoyl chloride to produce a 72% yield of 3'-O-benzoyl-6,1',6'-tri-O-tritylsucrose and 9% of the 2-O-benzoate derivative, and minor amounts of the 2,3'-dibenzoate derivative.

1,3-Diisothiocyanato-1,1,3,3-tetrabutyldistannoxane catalyzed transesterification reactions involving substrates such as benzyl alcohol and methyl butyrate are known. For instance, see the following references:

1) J. Otera, S. Ioka, and H. Nozaki, *J. Org. Chem.*, 54, 4013 (1989);

2) For chloro- and hydroxyl-substituted distannoxane transesterification catalysts, see J. Otera, T. Yano, A. Kawabata, and H. Nozaki, *Tetrahedron Lett.*, 2383 (1986); and 3) For synthetic applications in the natural products area, see S. Schreiber and H. Meyers, *J. Am. Chem. Soc.*, 110, 5198 (1988); and S. Schreiber, D. Desmaele, and J. Porco, *Tetrahedron Lett.*, 6689 (1988).

DETAILED DESCRIPTION OF THE INVENTION

The process of the invention comprises reacting sucrose with a carboxylic acid anhydride in a reaction mixture comprising a polar aprotic solvent and a catalytic quantity of a distannoxane diester, for a period of time and at a temperature sufficient to produce a sucrose-6-ester.

The process may be practiced in any of several different modes. The first mode simply involves dissolving sucrose and the requisite amount of DSDE catalyst in a polar aprotic solvent (mild heating usually required), and then treating the solution thus produced with a carboxylic acid anhydride at or slightly above room temperature. After the acylation is complete, the solution is treated with a small amount of water and the DSDE recovered for reuse by extraction. The acylation product mixture, which at this point consists primarily of sucrose-6-ester and lesser amounts of other sucrose monoesters, sucrose diesters, and residual sucrose in a medium consisting of polar aprotic solvent, carboxylic acid, and water, can then be freed of carboxylic acid and dried (e.g., by vacuum distillation) and subjected to chlorination to produce a 6-O-acyl-4,1',6'-trichloro-4,1',6'-trideoxygalactosucrose ("sucralose-6-ester") according to the teachings of Walkup et al., U.S. Pat. No. 4,980,463, cited above.

This mode of practice of the invention is illustrated in the Examples, e.g., Example 12.

Stoichiometric ratios (mol:mol) of tin diester catalyst ranging from 0.10 to 1.50 molar equivalent (basis sucrose) have been demonstrated, producing sucrose-6-ester yields ranging from about 35% to about 80+%. Laboratory data show that, up to approximately a sucrose:DSDE ratio of about 1:1, sucrose-6-ester yields increase as the stoichiometric amount of catalyst is increased. Both 1,3-diacetoxy-1,1,3,3-tetrabutyldistannoxane (distannoxane diacetate or "DSDA") and 1,3-dibenzoyloxy-1,1,3,3-tetrabutyldistannoxane (distannoxane dibenzoate or "DSDB") have been shown to be effective catalysts.

Polar aprotic solvents which have been employed include N,N-dimethylformamide ("DMF") and N-methyl-2-pyrrolidone ("NMP"). Other suitable solvents include dimethyl sulfoxide ("DMSO"), N,N-dimethylacetamide ("DMA"), and hexamethylphosphoramide ("HMPA"). When the DSDE concentration in the reaction mixture is high, it is advantageous to add a small amount (5–20 vol %) of a hydrocarbon-like cosolvent to keep it in solution. Useful cosolvents for this purpose include toluene, benzene, mixed xylenes, cyclohexane, methyl tert-butyl ether, chloroform, and the like.

Stoichiometric ratios of carboxylic acid anhydride ranging from about 1.00 to about 4.00 molar equivalents (basis sucrose) have demonstrated experimental utility. Preferred stoichiometric ratios are in the range of from about 1.10 to about 1.80 molar equivalents. Stoichiometric ratios below about 1.10 molar equivalents can lead to an undesirable amount of unreacted sucrose in the final product, while ratios above about 1.80 can cause the formation of undesired sucrose diesters.

Acylation reaction temperatures ranging from about 0° C. to about 60° C. have been found to be useful. The particular reaction temperature employed is not a narrowly critical aspect of the invention, although acylation reaction temperature affects the rate of acylation and excessively high temperatures can increase the production of undesirable sucrose esters. Preferred acylation temperatures range from about 20° C. to about 45° C. The acylation reaction will normally take from about ¼ hour to about 3 hours at the indicated temperature range of 0° to 60° C.

Both acetic anhydride and benzoic anhydride have been shown to be effective acylating agents. Acetic anhydride appears to be slightly superior. A variety of other carboxylic acid anhydrides would be expected to function effectively in the practice of the invention. Examples of such other anhydrides are the anhydrides of substituted benzoic acid (e.g., 4-nitrobenzoic acid, 3,5-dinitrobenzoic acid, and the like), alkanoic acids such as propionic acid, butyric acid, cyclohexane-carboxylic acid, long chain fatty acids, both saturated and unsaturated, such as stearic acid, oleic acid, linoleic acid, and the like, having up to, for example, 28 carbon atoms, unsaturated acids such as acrylic acid and methacrylic acid, substituted acids such chloroacetic acid, cyanoacetic acid, phenoxyacetic acid, and the like.

The rate of acylation is dependent upon a number of variables, which include catalyst stoichiometry (increasing catalyst concentration relative to sucrose increases the rate of acylation), activity of the catalyst (e.g., DSDA appears to be a more active catalyst than DSDB), reactivity of the carboxylic acid anhydride (e.g., acetic anhydride is more reactive than benzoic anhydride), and the reaction temperature and the relative concentration of the reactive species (as the acylation is a multi-order process).

DSDE may be recovered for reuse by the method of Vernon et al., U.S. Pat. No. 5,034,551. (In the present case, the DSDE may be used as recovered; Vernon et al. contemplated converting the DSDE to a distannoxane dialkoxide or a di(hydrocarbyl)tin oxide.) The acylation mixture is treated with a small amount of water and the DSDE is extracted in an essentially quantitative manner by contacting the mixture with a hydrocarbon such as toluene, cyclohexane, n-heptane, 2,2,4-trimethylpentane, or mixtures thereof, or an ether such as diethyl ether, di(n-propyl) ether, methyl tert-butyl ether, or the like. Recycling the DSDE is advantageous for economic reasons because a large proportion of the tin species can be recovered for reuse, and for processing reasons because solids handling is reduced (i.e., the DSDE is recovered in solution).

After removal of the DSDE for recycle, the reaction mixture contains sucrose-6-ester, carboxylic acid (that was formed by the reaction of carboxylic acid anhydride and sucrose plus any that might have been formed by the reaction of excess anhydride with the water that was added in the DSDE extraction step described above), some unreacted sucrose, a small amount of other sucrose esters, and polar aprotic solvent. It is preferred to remove the carboxylic acid from the solution of sucrose-6-ester in polar aprotic solvent prior to further processing of the sucrose-6-ester. This can be accomplished, for instance, by vacuum stripping when the acid is relatively volatile such as acetic acid. Make-up polar aprotic solvent may be added during the stripping operation, if it is desired to further process the sucrose-6-ester in the same solvent. (For example, if DMF is the solvent and chlorination via the Walkup et al. process will be the next step.) The desired sucrose-6-ester in residual polar aprotic solvent may then used directly in subsequent processing, or optionally it may be recovered by conventional procedures such as crystallization from a solvent such as methanol, as is illustrated by Example 15, below. The carbohydrate impurities that are usually present (unreacted sucrose and other sucrose esters) do not have an adverse affect on the chlorination of the sucrose-6-ester to produce sucralose-6-ester.

The second mode for the practice of the invention involves the use of a DSDE catalyst in a dehydrated or partially dehydrated reaction system, as is illustrated by, for instance, Examples 1–9. In this second mode, sucrose and a distannoxane diester are slurried in a reaction mixture comprising a mixed solvent system containing a polar aprotic solvent (as above) and a hydrocarbon-like cosolvent capable of removing any water present in the reaction mixture by codistillation. After removal of the water, the normally biphasic (but solids-free) reaction mixture is treated with a carboxylic acid anhydride within the temperature range taught above for the first mode. After the acylation is complete, the mixture is treated with a small amount of water and the DSDE recovered by extraction for reuse. The acylation product mixture may then be further processed (i.e., the water, carboxylic acid, and residual extraction solvent removed) and subjected to chlorination to make sucralose-6-ester.

In Example 10, for instance, 1.00 molar equivalent of sucrose and 1.05 molar equivalents of DSDA were slurried in an 8:3 (by volume) mixture of DMF and cyclohexane, and the mixture vigorously refluxed for 60 min in a reaction vessel equipped with a refluxive water separator. The solids-free reaction mixture was then cooled to ambient temperature and treated with 1.10 molar equivalents of acetic anhydride and stirred for about 18 hr. Following this, the reaction mixture was treated with water, extracted with cyclohexane (to recover DSDA), and partially evaporated to give a DMF-based syrup shown by HPLC analysis to contain an 82% yield of 6-O-acetylsucrose or sucrose-6-acetate.

Stoichiometric ratios (mol:mol) of DSDE catalyst ranging from 0.25 to 1.50 molar equivalents (basis sucrose) have been employed, producing sucrose-6-ester yields ranging from about 50% to over 80%. Laboratory data shows, up to a point [about 1:1], that sucrose-6-ester yields increase as the stoichiometric amount of catalyst is increased. Both fully and partially dehydrated DSDA and DSDB catalysts have proven effective, with other distannoxane diesters also expected to prove useful.

Cosolvents capable of codistillatively removing water include saturated hydrocarbons, aromatic hydrocarbons, chlorinated hydrocarbons, ketones, and ethers. A very wide range of solvents appear to be suitable for use as cosolvents in the invention. The primary criteria for a cosolvent are that it produce a mixture with the polar aprotic solvent, the DSDE, and the sucrose, that refluxes with an internal reaction temperature within the range of from about 75° C. to about 153° C. (and preferably less than 100° C. to minimize thermal degradation of sucrose), that it codistill the water present in the reaction mixture, and that it not render key reaction components (e.g., sucrose) insoluble.

Cosolvents which are immiscible with water and which do form a constant-composition minimum-boiling azeotrope with water are preferred, but the cosolvent does not have to be capable of forming a constant-boiling azeotrope of constant composition with water to be an effective cosolvent for the practice of the current invention. Nor is it necessary that the cosolvent be immiscible with water. It is necessary only that the cosolvent be capable of codistilling the water of hydration from the reaction medium.

Preferred cosolvents for reasons of chemical stability, efficiency of water removal, cost, and boiling point include toluene, cyclohexane, n-heptane, and isooctane (2,2,4-trimethylpentane). The preferred dehydration temperature is between the range of about 85° C. to about 100° C. Temperatures below about 85° C. can result in an unnecessarily slow dehydration, while temperature greater than about 100° C. can result in decomposition.

Dehydration temperatures are typically controlled in an empirical manner by adjusting the ratio of the polar aprotic solvent to the lower boiling cosolvent. Solvent to cosolvent ratios (by volume) of from about one-to-one to about ten-to-one are believed useful for the practice of this invention, with ratios of from about eight-to-five to about eight-to-one being preferred.

Solvent to cosolvent ratios are limited by practical considerations. Too much cosolvent will inhibit sucrose solubility and could produce a mixture with a boiling point too low for reasonable dehydration time. Too little cosolvent can limit the rate at which water can be codistilled from the reaction mixture, and can also result in dehydration temperatures high enough to cause thermal degradation of the carbohydrate species. Useful solvent:cosolvent proportions are usually found within the range of from about 3:1 to about 6:1 (wt:wt).

A wide range of solids (DSDE and sucrose) to solvents (polar aprotic solvent and cosolvent) ratios are useful for the practice of the invention. This is not considered to be a particularly critical aspect of the invention, provided that there is sufficient polar aprotic solvent present to insure the partial dissolution of the sucrose, and sufficient cosolvent present to insure water removal and to provide a desirable reaction temperature. Experimentally, solids-to-solvents ratios (wt/vol) of from about one-to-two to about one-to-six have demonstrated utility. The more concentrated systems are preferred for reasons of economics and practicality.

The reflux time required for the full or partial dehydration of mixtures of DSDE and sucrose is strictly a function of the efficiency of the removal of water from the system by codistillation. The efficiency of water removal from the reaction system is a function of a number of interactive variables. These variables, which to a large extent can be experimentally controlled, include: (a) the internal reaction temperature; (b) the boiling point of the cosolvent; (c) the water content of the codistillate; (d) the rate of heat input to the system; (e) the efficiency of agitation; and (f) the reactor configuration employed.

Full or partial reaction mixture dehydration times of from about 0.5 hr to about 8.0 hr have been found to be useful. The reflux period is terminated when the desired amount of water has been codistilled from the system. This determination is usually made by a water analysis of the distillate using the Karl Fischer method.

After completion of water removal, the normally biphasic (but solids-free) reaction mixtures are cooled to around room temperature and acylated as was described above for the first mode of practice of this invention. Recovery and reuse of the DSDE catalyst, and conversion of sucrose-6-ester to sucralose-6-ester may also be readily carried out as described above.

The examples below illustrate the practice of the invention.

EXAMPLE 1

The acetylation of sucrose by reaction with 0.25 equivalents of distannoxane diacetate (DSDA) and a 10% excess of acetic anhydride.

Sucrose (68.5 g, 200 mmol) was suspended in dimethylformamide (DMF, 400 ml) and a solution of DSDA in cyclohexane (17.41%, 172.2 g=50 mmol). The mixture was heated to boiling and allowed to distil at atmospheric pressure until the pot temperature reached 98° (distillate 80 ml, was removed). The mixture was then heated under reflux for 90 minutes, with azeotropic removal of the water formed in the reaction (Dean and Stark trap). The pot temperature dropped from 98° to 97° during this time and water (61.9 mmol) was evolved. The mixture was cooled to 20° and then acetic anhydride (22.5 g, 220 mmol) was added over 30 minutes. After stirring the mixture for 2 hours at ambient, water (25 ml) and cyclohexane (250 ml) were added, and the phases were separated. The DMF phase was extracted again with cyclohexane (250 ml) to remove DSDA. Hplc analysis of the DMF layer (505.9 g) revealed that the yield of sucrose-6-acetate was 49.6%; sucrose di-acetates made up 7.35% of the products and 22.4% of sucrose remained.

EXAMPLE 2

The acetylation of sucrose by reaction with 0.5 equivalents of distannoxane diacetate (DSDA) and a 10% excess of acetic anhydride.

Sucrose (68.5 g, 200 mmol) was suspended in dimethylformamide (DMF, 400 ml) and a solution of DSDA in cyclohexane (31.84%, 172.2 g=92 mmol). The mixture was heated to boiling and allowed to distil at atmospheric pressure until the pot temperature reached 99.5° (distillate 80 ml, was removed). The mixture was then heated under reflux for 90 minutes, with azeotropic removal of the water formed in the reaction (Dean and Stark trap). The pot temperature dropped from 99.5° to 98.5° during this time and water (107 mmol) was evolved. The mixture was cooled to 20° and then acetic anhydride (22.5 g, 220 mmol) was added over 30 minutes. After stirring the mixture for 2 hours at ambient, water (25 ml) and cyclohexane (500 ml) were added, and the phases were separated. The DMF phase was extracted again with cyclohexane (250 ml) to remove DSDA. Hplc analysis of the DMF layer (495.54 g) revealed that the yield of sucrose-6-acetate was 74.1%; sucrose di-acetates made up 13% the products and 6% of sucrose remained.

EXAMPLE 3

The acetylation of sucrose by reaction with 0.75 equivalents of distannoxane diacetate (DSDA) and a 10% excess of acetic anhydride.

Sucrose (68.5 g, 200 mmol) was suspended in dimethylformamide (DMF, 400 ml) and a solution of DSDA in cyclohexane (31.84%, 282.6 g≡150 mmol). The mixture was heated to boiling and allowed to distil at atmospheric pressure until the pot temperature reached 98° (distillate 150 ml, was removed). The mixture was then heated under reflux for 90 minutes, with azeotropic removal of the water formed in the reaction (Dean and Stark trap). The pot temperature dropped from 98° to 97° during this time and water (139 mmol) was evolved. The mixture was cooled to 20° and then acetic anhydride (22.5 g, 220 mmol) was added over 23 minutes. After stirring the mixture for 2 hours at ambient, water (25 ml) and cyclohexane (500 ml) were added, and the phases were separated. The DMF phase was extracted again with cyclohexane (250 ml) to remove DSDA. Hplc analysis of the DMF layer (487.95 g) revealed that the yield of sucrose-6-acetate was 78%; the yield of sucrose di-acetates was 12.2%, and the level of residual sucrose was 2.7%.

EXAMPLE 4

The acetylation of sucrose by reaction with 1.0 equivalents of distannoxane diacetate (DSDA) and a 10% excess of acetic anhydride.

Sucrose (45 g, 131.5 mmol) was suspended in dimethylformamide (DMF, 281 ml) and a solution of DSDA in cyclohexane (24.12%, 327.1 g≡131.5 mmol). The mixture was heated to boiling and allowed to distil at atmospheric pressure until the pot temperature reached 98°. The mixture was then heated under reflux for 90 minutes, with azeotropic removal of the water formed in the reaction (Dean and Stark trap). The pot temperature dropped from 98° to 96° during this time and water (104 mmol) was evolved. The mixture was cooled to 20° and then acetic anhydride (14.76 g, 144.6 mmol) was added over 15 minutes. After stirring the mixture for 2 hours at ambient, water (16.4 ml) and cyclohexane (328 ml) were added, and the phases were separated. The DMF phase was extracted again with cyclohexane (164 ml) to remove DSDA. Hplc analysis of the DMF layer (317.7 g) revealed that the yield of sucrose-6-acetate was 75.3%; the yield of sucrose di-acetates was 13.7%, and the level of residual sucrose was 1.2%.

EXAMPLE 5

The acetylation of sucrose by reaction with 1.5 equivalents of distannoxane diacetate (DSDA) and a 10% excess of acetic anhydride.

Sucrose (68.5 g, 200 mmol) was suspended in dimethylformamide (DMF, 400 ml) and a solution of DSDA in cyclohexane (56.96%, 316 g≡300 mmol). The mixture was heated to boiling and allowed to distil at atmospheric pressure until the pot temperature reached 98°. The mixture was then heated under reflux for 90 minutes, with azeotropic removal of the water formed in the reaction (Dean and Stark trap). Water (176 mmol) was evolved during this time. The mixture was cooled to 20° and then acetic anhydride (22.5 g, 220 mmol) was added over 23 minutes. After stirring the mixture for 2 hours at ambient, water (25 ml) and cyclohexane (750 ml) were added, and the phases were separated. The DMF phase was extracted again with cyclohexane (250 ml) to remove DSDA. Hplc analysis of the DMF layer (506.94 g) revealed that the yield of sucrose-6-acetate was 81.6%; the yield of sucrose di-acetates was 12.2%, and the level of residual sucrose was 1.5%.

EXAMPLE 6

The acetylation of sucrose employing recycled DSDA (1.05 equivalents) and a 10% excess of acetic anhydride.

Sucrose (68.5 g, 200 mmol) and DMF (400 ml) were added to a solution of DSDA in cyclohexane (about 25% w/w, containing 210 mmol of DSDA), which had been used once already in a sucrose-6-acetate preparation. The mixture was distilled until the temperature rose to 98°, and was then heated under reflux with stirring for 90 minutes (Dean and Stark trap). The reaction solution was then cooled to 20° and acetic anhydride (22.5 g, 220 mmol) was added over 20 to 30 minutes. After the addition the mixture was stirred at ambient for 2 hours, when water (25 ml) and cyclohexane (500 ml) were added. The phases were separated and the heavier DMF layer was extracted again with cyclohexane (250 ml). The extracts were combined and concentrated to about 25% solids for the next cycle. A small make-up of DSDA (1.5% of the original charge) was added at this point, and the reaction set forth above was repeated. Five more experiments were carried out in this sequence, and the DMF layers from each cycle were analyzed, with the following results:

| Cycle # | DMF layer g | Molar yield % Suc-6-acetate | % recovery Diacetates | % recovery sucrose |
| --- | --- | --- | --- | --- |
| 1 | 488.78 g | 74.18 | 13.35 | 2.62 |
| 2 | 496.57 g | 81.72 | 12.56 | 2.12 |
| 3 | 495.82 g | 79.73 | 14.26 | 1.35 |
| 4 | 500.62 g | 80.9 | 13.4 | 2.3 |
| 5 | 496.97 g | 78.19 | 13.4 | 1.5 |
| 6 | 511.15 g | 83.62 | 14.06 | 1.65 |

EXAMPLE 7

The acetylation of sucrose employing DSDA (1.05 equivalents) and a 10% excess of acetic anhydride (30 minute first step).

A 200 mmol-scale reaction was carried out as in example 6, but the period of heating under reflux was cut to 30 minutes. Water (84 mmol) was evolved in the reaction. The yield of sucrose-6-acetate was 72.1%; diacetates were produced in 14.8% yield, and the level of residual sucrose was 5.2%.

EXAMPLE 8

The acetylation of sucrose employing DSDA (1.05 equivalents) and a 10% excess of acetic anhydride (60 minute first step).

A 200 mmol-scale reaction was carried out as in example 6, but the period of heating under reflux was cut to 60 minutes. Water (150 mmol) was evolved in the reaction. The yield of sucrose-6-acetate was 79.8%; diacetates were produced in 10.5% yield, and the level of residual sucrose was 3.9%.

EXAMPLE 9

The acetylation of sucrose employing DSDA (1.05 equivalents) and a 10% excess of acetic anhydride (75 minute first step).

A 200 mmol-scale reaction was carried out as in example 6, but the period of heating under reflux was cut to 75 minutes. Water (144 mmol) was evolved in the reaction. The yield of sucrose-6-acetate was 80.8%; diacetates were produced in 11.7% yield, and the level of residual sucrose was 1.5%.

EXAMPLE 10

A 1000-ml, three-neck, round-bottom flask, equipped with mechanical stirrer, thermometer, and Dean-Stark water separator, topped with a reflux condenser, was charged with 68.5 g (200 mmol) of sucrose, 126 g (210 mmol) of DSDA, 400 ml of DMF, and 150 ml of cyclohexane. The slurry was heated to reflux (95° C. reaction temperature), and the resulting solids-free mixture refluxed for 60 min. The contents of the water separator were removed, dissolved in anhydrous isopropanol, and assayed for water by the Karl Fischer method (2.32 g, 129 mmol).

The solids-free mixture was cooled to about 20° C., and treated dropwise over about 3 min with 22.5 g (220 mmol) of acetic anhydride. During the anhydride addition, ice-bath cooling was used as needed to keep the reaction temperature below 25° C. After stirring overnight at room temperature, the reaction mixture was worked-up as described in Example 5 to provide a syrup shown by HPLC analysis to contain 62.9 g (164 mmol, 82.0% yield) of sucrose-6-acetate.

EXAMPLE 11

The acetylation of sucrose catalyzed by DSDA (1.05 equivalents) in DMF solution.

A solution of DSDA in cyclohexane (25.36%, 496.8 g=210 mmol) was distilled to remove solvent (325 ml) and then DMF (400 ml) was added. The solution was distilled until the pot temperature rose to 153° and was then cooled to 25°. Sucrose (68.5 g, 200 mmol) and DMF (300 ml) were then added and when all solids had dissolved, acetic anhydride (22.5 g, 220 mmol) was added over 65 minutes. After 6.5 hours hplc analysis revealed that the yield of sucrose-6-acetate was 60% and the level of residual sucrose was 9.3%; di-acetates made up 17.4% of the products.

EXAMPLE 12

The acetylation of sucrose catalyzed by DSDA (2.1 equivalents) in DMF solution.

A solution of recycled DSDA in cyclohexane (22.6%, 278.48 g=105 mmol) was concentrated to a thick syrup under reduced pressure at 40°. DMF (200 ml) was then added, and evaporation was continued to remove all of the cyclohexane. Sucrose (17.15 g, 50mmol) and DMF (200 ml) were then added and when all solids had dissolved, acetic anhydride (5.62 g, 55 mmol) was added over 40 minutes at 25°. After 6 hours the yield of sucrose-6-acetate was 65% and the level of residual sucrose was 8.1%; di-acetates made up 14.4% of the products.

EXAMPLE 13

The acetylation of sucrose catalyzed by DSDA (0.5 equivalents) in DMF solution.

A solution of DSDA in cyclohexane (31.84%, 94.2 g=50mmol) was concentrated to a thick syrup under reduced pressure at 40°. DMF (200 ml) was then added, and evaporation was continued to remove traces of cyclohexane. Sucrose (34.25 g, 100 mmol) and DMF (100 ml) were then added and when all solids had dissolved, acetic anhydride (11.23 g, 110 mmol) was added over 65 minutes at ambient temperature. After 6 hours the yield of sucrose-6-acetate was 55% and the level of residual sucrose was 14.2%; diacetates made up 15.8% of the products.

EXAMPLE 14

The acetylation of sucrose catalyzed by distannoxane dibenzoate (DSDB 1.05 equivalents) in DMF solution.

To a solution of DSDB in DMF (27.27%, 100 g=37.66 mmol) was added sucrose (12.3 g, 36 mmol) and DMF (50 ml). When all the solids had dissolved, acetic anhydride (4.04 g, 39.6 mmol) was added over 12 minutes at ambient temperature. After 7 hours the yield of sucrose-6-acetate was 55.6%; di-acetates were at 16.9%, and 21.6% of sucrose had not undergone reaction.

EXAMPLE 15

Crystalline sucrose-6-acetate by the DSDA route.

The DMF layers from two 200 mmol-sucrose scale reactions (first step 90 minute reflux, 2 hour acetylation) were combined and concentrated to 259.24 g, under reduced pressure at 45°, which removed the acetic acid as well as most of the DMF. The dark syrup was dissolved in warm methanol (350 ml) and set aside to crystallize overnight. The product was collected, washed with methanol (200 ml) and dried in vacuo at 45°. Yield 98.65 g (56.4% molar); assay, sucrose-6-acetate, 87.84%; sucrose, 1.5%; di-acetates, 3.17%; methanol 7.72%.

EXAMPLE 16

Sucralose-6-acetate from sucrose-6-acetate

The crude sucrose-6-acetate product in DMF (total 485 g) from a 200 mmol-sucrose scale reaction, which had been prepared as in example 6 was concentrated at 50° to 60° under reduced pressure to remove acetic acid and water. The concentrated dark syrup (103 g) [assay, sucrose-6-acetate, 57.83%; sucrose mono-acetates, 4.23%; di-acetates, 11.37%; sucrose, 1.02%], was dissolved in DMF (325 ml) and the solution was cooled to 0°. Vilsmeier reagent (203.4 g) was then added and the suspension was warmed to 115° over 45 minutes and held at that temperature for 2.5 hours. The mixture was then cooled to −5°, when an ice-cold aqueous solution of sodium hydroxide (12%, 503 g) was added. The temperature of the mixture rose to 55° before subsiding, and a few drops of concentrated hydrochloric acid were added to adjust the pH of the mixture to neutrality. Hplc analysis of the quenched reaction mixture revealed that sucralose-6-acetate (37.5 g, 55% yield) had been formed.

EXAMPLE 17

PREPARATION OF SUCROSE-6-ACETATE USING 0.25 EQUIVALENT DISTANNOXANE DIACETATE

A 1000-ml, three-neck, round-bottom flask, equipped with mechanical stirrer, thermometer, and 60-ml dropping funnel topped with an argon inlet, was charged with 68.5 g (200 mmol) of sucrose, 30.6 g (51 mmol) of DSDA, and 500 ml of DMF. The suspension was heated at 75° C. (internal temperature) for 10 min, and the clear solution thus produced cooled to room temperature and treated dropwise over 15 min with 22.5 g (220mmol) of acetic anhydride dissolved in 50 ml of DMF. The anhydride addition produced a mild (less than 5° C.) exotherm.

After stirring overnight at room temperature under argon, the reaction mixture was treated with water (50 ml), extracted with cyclohexane (2×500 ml) to remove DSDA, and the DMF evaporated (rotary evaporator, mechanical-pump vacuum, 30° C. water bath) to afford a pale-yellow syrup determined by HPLC analysis to contain 42.7 g (111 mmol, 55.6% yield) of sucrose-6-acetate.

EXAMPLE 18

PREPARATION OF SUCROSE-6-BENZOATE USING 0.25 EQUIVALENT DISTANNOXANE DIACETATE

The experiment of Example 17 was repeated using 49.8 g (220 mmol) of benzoic anhydride for acylation. After stirring for three days, the reaction was worked-up to give a viscous oil determined by HPLC analysis to contain 40.6 g (90.9 mmol, 45.4% yield) of sucrose-6-benzoate.

EXAMPLE 19

PREPARATION OF SUCROSE-6-BENZOATE USING 0.25 EQUIVALENT DISTANNOXANE DIBENZOATE

The experiment of Example 18 was repeated using 37.1 g (51 mmol) of DSDB as catalyst. After stirring at room temperature under argon for three days, the reaction was worked-up to produce a syrup determined by HPLC analysis to contain 36.8 g (82.5mmol, 41.3% yield) of sucrose-6-benzoate.

EXAMPLE 20

PREPARATION OF SUCROSE-6-ACETATE USING 0.25 EQUIVALENT DISTANNOXANE DIBENZOATE

The experiment of Example 17 was repeated with 34.2 g (100 mmol) of sucrose, 18.6 g (25.6 mmol) of DSDB, 250 ml of DMF, and 11.2 g (110 mmol) of acetic anhydride to give a viscous oil determined by HPLC analysis to contain 21.0 g (54.6 mmol, 54.6% yield) of sucrose-6-acetate.

EXAMPLE 21

PREPARATION OF SUCROSE-6-BENZOATE USING 0.50 EQUIVALENT DISTANNOXANE DIACETATE

The experiment of Example 17 was repeated using 49.8 g (220 mmol) of benzoic anhydride for acylation. After stirring for two days at room temperature under argon, the reaction was worked-up to produce a viscous oil determined by HPLC analysis to contain 56.3 g (126 mmol, 63.0%) of sucrose-6-benzoate.

EXAMPLE 22

PREPARATION OF SUCROSE-6-ACETATE USING 0.50 EQUIVALENT 1,3-DIACETOXY-1,1,3,3-TETRAOCTYLDISTANNOXANE

Tetraoctyldistannoxane diacetate monohydrate was prepared by dissolving 37.9 g (103 mmol) of dioctyltin oxide ("DOTO") in 400 ml of glacial acetic acid at 80° C. (about 15 min required). Rotary evaporation (water-aspirator vacuum, 65° C. water bath) afforded the product as a pale-yellow viscous oil. The oil was dissolved in 500 ml of DMF, and the solution partially evaporated (rotary evaporator, mechanical-pump vacuum, 30° C. water bath) to remove the residual acetic acid (final volume about 300 ml). The yield was assumed to be quantitative (43.0 g, 50.0 mmol).

The experiment of Example 17 was repeated using the above-described DMF solution of the tetraoctyl derivative, 34.2 g (100 mmol) of sucrose, and 11.2 g (110 mmol) of acetic anhydride. After stirring overnight at room temperature under argon, the reaction mixture was worked-up to give a syrup shown by HPLC assay to contain 25.4 g (66.1 mmol, 66.1% yield) of sucrose-6-acetate.

EXAMPLE 23

PREPARATION OF SUCROSE-6-ACETATE IN N-METHYL-2-PYRROLIDONE SOLVENT USING 0.50 EQUIVALENT DISTANNOXANE DIACETATE

DSDA was prepared by dissolving 51.6 g (200 mmol) of DBTO in 400 ml of glacial acetic acid at room temperature (about 5 min required). Rotary evaporation (water-aspirator vacuum, 50° C. water bath) provided the product as a colorless viscous oil. The oil was dissolved in 750 ml of NMP, and the solution partially evaporated (rotary evaporator, mechanical-pump vacuum, 50° C. water bath) to remove the residual acetic acid (final volume about 500 ml). The yield was assumed to be quantitative (61.2 g, 100 mmol).

The experiment of Example 18 was repeated using the above-described NMP solution. After stirring at room temperature overnight, the reaction mixture was worked-up to afford a syrup shown by HPLC analysis to possess 40.1 g (104 mmol, 52.2% yield) of sucrose-6-acetate.

EXAMPLE 24

PREPARATION OF SUCROSE-6-BENZOATE USING 1.05 EQUIVALENTS DISTANNOXANE DIACETATE WITH DEHYDRATION

The experiment of Example 10 was repeated using 49.8 g (210 mmol) of benzoic anhydride for acylation. The dehydration temperature was 95° C. (60-min reflux). Work-up afforded a syrup containing 65.9 g (148 mmol, 73.8% yield) of sucrose-6-benzoate.

What is claimed is:

1. A process which comprises reacting sucrose with a carboxylic acid anhydride in a reaction mixture consisting essentially of a first solvent comprising a polar aprotic solvent and a catalytic quantity of a 1,3-diacyloxy-1,1,3,3-tetra(hydrocarbyl)distannoxane, for a period of time within the range of from about ¼ hour to about 3 hours and at a temperature within the range of from about 0° C. to about 60° C., said time and temperature being sufficient to produce a sucrose-6-ester.

2. The process of claim 1 wherein the 1,3-diacyloxy-1,1,3,3-tetra(hydrocarbyl)distannoxane is a 1,3-diacyloxy-1,1,3,3-tetra(alkyl)distannoxane selected from the group consisting of 1,3-diacetoxy-1,1,3,3-tetra(alkyl)distannoxane and 1,3-dibenzoyloxy-1,1,3,3-tetra(alkyl)distannoxane.

3. The process of claim 2 wherein the 1,3-diacyloxy-1,1,3,3-tetra(alkyl)distannoxane is 1,3-diacetoxy-1,1,3,3-tetrabutyldistannoxane, 1,3-diacetoxy-1,1,3,3-tetraoctyldistannoxane, 1,3-dibenzoyloxy-1,1,3,3-tetrabutyldistannoxane or 1,3-dibenzoyloxy-1,1,3,3-tetraoctyl distannoxane, and wherein the carboxylic acid anhydride is acetic anhydride or benzoic anhydride.

4. The process of claim 3 wherein the 1,3-diacyloxy-1,1,3,3-tetra(alkyl)distannoxane is 1,3-diacetoxy-1,1,3,3-tetrabutyldistannoxane.

5. The process of claim 4 wherein the polar aprotic solvent is N,N-dimethylformamide.

6. The process of claim 5 wherein the carboxylic acid anhydride is acetic anhydride.

7. The process of claim 6 wherein said process includes the step of removing acetic acid from the solution of sucrose-6-ester in polar aprotic solvent, said acetic acid having been formed by reaction of acetic anhydride with sucrose.

8. The process of claim 4 wherein the carboxylic acid anhydride is acetic anhydride.

9. The process of claim 1 wherein the polar aprotic solvent is N,N-dimethylformamide.

10. The process of claim 1 wherein the carboxylic acid anhydride is acetic anhydride.

11. The process of claim 1 wherein the reaction mixture additionally includes a second solvent capable of removing water by codistillation, and wherein the process includes the step of codistillation to remove water from the reaction mixture.

12. The process of claim 11 wherein the second solvent is a member selected from the group consisting of hydrocarbons, chlorinated hydrocarbons, ketones, and ethers.

13. The process of claim 12 wherein the second solvent is a member selected from the group consisting of toluene, cyclohexane, n-heptane, and isooctane.

14. The process of claim 11 wherein the 1,3-diacyloxy-1,1,3,3-tetra(hydrocarbyl)distannoxane is a member selected from the group consisting of 1,3-diacetoxy-1,1,3,3-tetrabutyldistannoxane, 1,3-dibenzoyloxy-1,1,3,3-tetrabutyldistannoxane, 1,3-diacetoxy-1,1,3,3-tetraoctyldistannoxane, and 1,3-dibenzoyloxy-1,1,3,3-tetraoctyldistannoxane, wherein the first solvent is N,N-dimethylformamide, and wherein the carboxylic acid anhydride is acetic anhydride or benzoic anhydride.

15. The process of claim 14 wherein the second solvent is a member selected from the group consisting of toluene, cyclohexane, n-heptane, and isooctane.

16. The process of claim 14 wherein the carboxylic acid anhydride is acetic anhydride and the 1,3-diacyloxy-1,1,3,3-tetra(hydrocarbyl)distannoxane is a 1,3-diacetoxy-1,1,3,3-tetra(alkyl)distannoxane.

17. The process of claim 16 wherein said process includes the step of removing acetic acid from the solution of sucrose-6-ester in polar aprotic solvent, said acetic acid having been formed by reaction of acetic anhydride with sucrose.

18. The process of claim 11 wherein said process includes the step of removing carboxylic acid from the solution of sucrose-6-ester in polar aprotic solvent, said carboxylic acid having been formed by reaction of carboxylic acid anhydride with sucrose.

19. The process of claim 1 wherein said process includes the step of removing carboxylic acid from the solution of sucrose-6-ester in polar aprotic solvent, said carboxylic acid having been formed by reaction of carboxylic acid anhydride with sucrose.

20. A process which comprises:
(1) preparing a solution of sucrose and a 1,3-diacyloxy-1,1,3,3-tetra(hydrocarbyl)distannoxane in a polar aprotic solvent to form a first reaction mixture; and
(2) adding a carboxylic acid anhydride to said first reaction mixture to form a second reaction mixture and maintaining said second reaction mixture at a temperature and for a period of time sufficient to produce a sucrose-6-ester.

21. The process of claim 20 wherein the 1,3-diacyloxy-1,1,3,3-tetra(hydrocarbyl)distannoxane is a 1,3-diacyloxy-1,1,3,3-tetra-(alkyl)distannoxane selected from the group consisting of 1,3-diacetoxy-1,1,3,3-tetra(alkyl)distannoxane and 1,3-dibenzoyloxy-1,1,3,3-tetra(alkyl)distannoxane.

22. The process of claim 21 wherein the 1,3-diacyloxy-1,1,3,3-tetra(alkyl)distannoxane is 1,3-diacetoxy-1,1,3,3-tetrabutyldistannoxane, 1,3-diacetoxy-1,1,3,3-tetraoctyldistannoxane, 1,3-dibenzoyloxy-1,1,3,3-tetrabutyldistannoxane or 1,3-dibenzoyloxy-1,1,3,3-tetraoctyl distannoxane.

23. The process of claim 22 wherein the 1,3-diacyloxy-1,1,3,3-tetra(alkyl)distannoxane is 1,3-diacetoxy-1,1,3,3-tetrabutyldistannoxane.

24. The process of claim 23 wherein the polar aprotic solvent is N,N-dimethylformamide.

25. The process of claim 24 wherein the carboxylic acid anhydride is acetic anhydride.

26. The process of claim 23 wherein the carboxylic acid anhydride is acetic anhydride.

27. The process of claim 26 wherein said process includes the step of removing acetic acid from the solution of sucrose-6-ester in polar aprotic solvent, said acetic acid having been formed by reaction of acetic anhydride with sucrose.

28. The process of claim 20 wherein the polar aprotic solvent is N,N-dimethylformamide.

29. The process of claim 20 wherein the carboxylic acid anhydride is acetic anhydride.

30. The process of claim 20 wherein said process includes the step of removing carboxylic acid from the solution of sucrose-6-ester in polar aprotic solvent, said carboxylic acid having been formed by reaction of carboxylic acid anhydride with sucrose.

31. The process of claim 20 wherein said temperature is within the range of from about 0° C, to about 60° C. and said period of time is within the range of from about ¼ hour to about 3 hours.

32. A process which comprises:
(1) preparing a first reaction mixture comprising sucrose, a polar aprotic solvent, a second solvent capable of removing water by codistillation, and a 1,3-diacyloxy-1,1,3,3-tetra(hydrocarbyl)distannoxane;
(2) subjecting said first reaction mixture to codistillation to remove water, to form thereby a second reaction mixture; and (3) adding a carboxylic acid anhydride to said second reaction mixture to form a third reaction mixture and maintaining said third reaction mixture at a temperature and for a period of time sufficient to produce a sucrose-6-ester.

33. The process of claim 32 wherein the second solvent is a member selected from the group consisting of hydrocarbons, chlorinated hydrocarbons, ketones, and ethers.

34. The process of claim 33 wherein the second solvent is a member selected from the group consisting of toluene, cyclohexane, n-heptane, and isooctane.

35. The process of claim 32 wherein the 1,3-diacyloxy-1,1,3,3-tetra(hydrocarbyl)distannoxane is a member selected from the group consisting of 1,3-diacetoxy-1,1,3,3-tetrabutyldistannoxane, 1,3-dibenzoyloxy-1,1,3,3-tetrabutyldistannoxane, 1,3-diacetoxy-1,1,3,3-tetraoctyldistannoxane, and 1,3-dibenzoyloxy-1,1,3,3-tetraoctyldistannoxane, wherein the polar aprotic solvent is N,N-dimethylformamide, and wherein the carboxylic acid anhydride is acetic anhydride or benzoic anhydride.

36. The process of claim 35 wherein the second solvent is a member selected from the group consisting of toluene, cyclohexane, n-heptane, and isooctane.

37. The process of claim 36 wherein the carboxylic acid anhydride is acetic anhydride.

38. The process of claim 37 wherein said process includes the step of removing acetic acid from the solution of sucrose-6-ester in polar aprotic solvent, said acetic acid having been formed by reaction of acetic anhydride with sucrose.

39. The process of claim 32 wherein said process includes the step of removing carboxylic acid from the solution of sucrose-6ester in polar aprotic solvent, said carboxylic acid having been formed by reaction of carboxylic acid anhydride with sucrose.

40. The process of claim 32 wherein said temperature is within the range of from about 0° C. to about 60° C. and said period of time is within the range of from about ¼ hour to about 3 hours.

* * * * *